United States Patent [19]

Nakatsu et al.

[11] Patent Number: 5,453,276

[45] Date of Patent: Sep. 26, 1995

[54] ANTIMICROBIAL COMPOSITIONS OF INDOLE AND NATURALLY OCCURRING ANTIMICROBIALS

[75] Inventors: Tetsuo Nakatsu, Walnut Creek; Kok Lean Raphael Kang, Oakland; Randi L. Helms, Martinez; Jiansheng Huang, Concord, all of Calif.

[73] Assignees: Takasago International Corporation, Tokyo, Japan; Takasago Institute for Interdisciplinary Science, Inc., Walnut Creek, Calif.

[21] Appl. No.: 147,913

[22] Filed: Nov. 4, 1993

Related U.S. Application Data

[63] Continuation of Ser. No. 832,926, Feb. 10, 1992, abandoned.

[51] Int. Cl.[6] .................................................. A01N 25/02
[52] U.S. Cl. ................................................ 424/405; 424/409
[58] Field of Search ................................ 424/404, 405

[56] References Cited

U.S. PATENT DOCUMENTS 4,855,127  8/1989  Abrutyn et al. ..................... 424/411

FOREIGN PATENT DOCUMENTS 1245058  9/1989  Japan .

OTHER PUBLICATIONS

Christensen, *Toxic Substances List,* 1973 p. 531 Indole.
Abstract by Biojis: Himejima M. & Kubo I. in J. Agric. Food Chem 39(2) 1991 418–421–Antibacterial Agents from Cashew An Acardium.
Martindale—The Extra Pharmacopoeia p. 257 26th Edition 1972.
Wilson et al.—Textbook of Organic Medicinart Pharmaceutical Chemistry—2nd edition pp. 215 & 767.
Chem Abstracts: Propolis–vol. 112 #12; 100103k p. 62 Mizuno.
Chem Abstracts: Topical Treatment of Acne—vol. 97 #11 Gloot et al. #84841p p. 44.

*Primary Examiner*—Thurman K. Page
*Assistant Examiner*—Neil Levy
*Attorney, Agent, or Firm*—Spensley Horn Jubas & Lubitz

[57] ABSTRACT

Antimicrobial compositions for controlling *P. aeruginosa* or *P. acnes* which contains indole and a naturally occurring substance selected from the group consisting of anacardic acid, limonene, β-pinene, farnesol, β-citronellol, pine resin, hinokitiol, longifolene, and β-caryophyllene.

2 Claims, No Drawings

ANTIMICROBIAL COMPOSITIONS OF INDOLE AND NATURALLY OCCURRING ANTIMICROBIALS

This is a continuation of application Ser. No. 07/832,926 filed on Feb. 10, 1992, now abandoned.

BACKGROUND OF THE INVENTION

1. Field of the Invention

This invention relates to an antimicrobial composition comprising indole and selected naturally occurring substances whose combination shows greater antimicrobial activity, particularly against *P. aeruginosa* and/or against *P. acnes* than does each component alone.

2. Description of the Prior Art

Microorganisms contaminate foodstuffs, cosmetics, and pharmaceutical products. Currently available disinfectants to control such harmful microorganisms are hinokitiol, benzoic acid (or its sodium salt), salicylic acid, p-hydroxybenzoic acid, etc.

Despite the wide use of these disinfectants, they do not appear to be effective against certain bacteria, particularly *Pseudomonas aeruginosa* (*P. aeruginosa*). *P. aeruginosa* is noted as a pathogen which causes serious infections in hospitals, clinics and at home. Although such disinfectants as o-phenylphenol and tert-alkyl ammonium salts are especially being used to control *P. aeruginosa*, they do not effectively inhibit the microorganism.

Accordingly, there is a definite need for antimicrobial compositions that are effective against *P. aeruginosa* and are safe for continuous and repetitive use.

Acne vulgaris is a common skin disorder. The typical skin lesions include blackheads (open comedones), whiteheads (closed comedones), and localized areas of inflammation (papules and pustules). The areas of skin commonly affected by acne are face, chest and upper back, where pilosebaceous units are concentrated. It is believed that *Propionibacterium aches* (*P. acnes*) plays a key role in the pathogenesis of acne. This bacterium resides in the pilosebaceous canal and produces a lipase that hydrolyzes triglycerides to free fatty acids in sebum. The free fatty acids thus generated are believed to cause both inflammation and comedones.

Currently, several medicaments are available to treat acne. These medicaments include benzoyl peroxide; retinoic acid; antibiotics such as tetracycline and erythromycin; and estrogens such as ethinyl estradiol. None of these drugs is completely free from side effects. For example, upon application of retinoic acid, erythema and exfoliation are commonly observed. Retinoic acid is also known to cause increased incidence of cutaneous tumors in experimental animals which receive the topical application of retinoic acid followed by UV light exposure.

Accordingly, a search continues for more improved antimicrobial compositions that are effective against *P. acnes* and are safe for continuous and repetitive use as an anti-acne agent.

The present combination of indole with one or more naturally occurring substances provides desirable enhancement in the antimicrobial activity of the naturally occurring substances.

SUMMARY OF THE INVENTION

In accordance with the present invention, it has now been found that indole enhances the antimicrobial activities of certain naturally occurring substances which themselves are ineffective or only show some degree of activity against various bacteria including *P. aeruginosa* and/or against *P. acnes*.

In one aspect of the present invention, there is provided an antimicrobial composition against *P. aeruginosa* comprising:

(a) an effective amount of a naturally occurring substance selected from the group consisting of anacardic acid, limonene, β-pinene, farnesol, citronellol, and pine resin; and (b) indole in an amount sufficient to enhance the antimicrobial activity of the naturally occurring substance.

The present invention further provides a cosmetic product comprising the above-defined antimicrobial composition.

The present invention also provides a disinfectant comprising the above-defined antimicrobial composition.

In another aspect of the present invention, there is provided an antimicrobial composition against *P. acnes* comprising:

(a) an effective amount of a naturally occurring substance selected from the group consisting of anacardic acid, β-caryophyllene, citronellol, farnesol, limonene, longifolene, and β-pinene; and (b) indole in an amount sufficient to enhance the antimicrobial activity of the naturally occurring substance.

The present invention further provides a cosmetic or pharmaceutical product comprising the above-defined anti-acne composition.

DETAILED DESCRIPTION OF THE INVENTION

One constituent of the antimicrobial composition of the present invention is indole. Indole is used as a flavoring agent in various types of foods such as beverages and ice creams. The antibacterial and antifungal activity of indole has been reported by Oimomi et al., *J. Antibiotics*, 27, 987 (1974). However, the reported activities are very weak (>400 µg/ml), including the activity against *P. aeruginosa*.

The other constituent of the antimicrobial composition is selected from known naturally occurring substances. Suitable substances which can be employed in combination with indole are anacardic acid [The Merk Index, 11th Ed., monograph no. 657], farnesol [The Merk Index, 11th Ed., monograph no. 3875], hinokitiol [CAS 499-44-5], β-pinene [The Merk Index, 11th Ed., monograph no. 7320], β-citronell [The Merk Index, 11th Ed., monograph no. 2332], β-caryophyllene [The Merk Index, 11th Ed., monograph no. 1857], longifolene [The Merk Index, monograph no. 5446], limonene [The Merk Index, monograph no. 5321], and pine resin [R. Fujii et al., *Phytochemistry*, 23, 875 (1984)]. These naturally occurring substances are relatively abundant in nature and easily available from their natural sources.

It will be appreciated that many other known naturally occurring substances may be used in this invention. However, the individually named naturally occurring substances are particularly preferred because of their greater effectiveness relative to other substances not named individually.

Some of the naturally occurring substances used in the present invention are known to possess antimicrobial activities. For example, anacardic acids have been reported to inhibit the growth of microorganisms, [M. Himejima et al., *J. Argic. Food Chem.*, 39, 418 (1991)]. However, their antimicrobial activity is not potent enough to be antimicrobial agents for many bacteria, including *P. aeruginosa*.

There have been no reports concerning the combination of indole and the above-enumerated naturally occurring substances for purposes of synergistically increasing the antimicrobial activities of the respective constituents which are otherwise weak in antimicrobial activity.

Many of the naturally occurring substances which can be used in this invention have been accepted as flavoring agents or fragrances. Thus, they are considered safe for use in cosmetics, household products, and foodstuffs.

A preferred embodiment of this invention is a composition comprising indole and anacardic acid, since the combination shows especially increased activity against *P. aeruginosa*. Another preferable combination is a composition comprising indole and pine resin.

A further preferred embodiment of this invention is a composition comprising indole and a member selected from limonene, β-pinene, longifolene, or β-caryophyllene, since each combination shows especially increased activity against *P. acnes*.

The naturally occurring substances used in this invention are present in the composition in an antimicrobially effective amount. As employed herein, the term "effective amount" denotes an amount sufficient to kill or inhibit *P. aeruginosa* or *P. acnes*. Thus, the term not only applies to microbicidal (killing) activity, but also to microbistatic (inhibiting) activity.

In general, the amount of indole to be used for enhancing the antimicrobial activity of the naturally occurring substances against *P. aeruginosa* or *P. acnes* can vary over a wide range. In the case of an antimicrobial composition against *P. aeruginosa*, optimum antimicrobial results are obtained with from about 5 to about 0.01 parts by weight of the naturally occurring substances to about one part by weight of indole. Thus, weight ratios of indole to the naturally occurring substances of from 0.2:1 to 100:1 can be used in this invention.

In the case of an antimicrobial composition against *P. acnes*, optimum antimicrobial results are obtained with from about 1 to about 0.001 parts by weight of the naturally occurring substances to about one part by weight of indole. Thus, weight ratios of indole to the naturally occurring substances of from 1:1 to 1000:1 can be used in the anti-acne compositions.

When contemplating the use of an antimicrobial composition of this invention against *P. aeruginosa*, the composition may include acceptable carriers and diluents for its intended use. Suitable carrier and diluents include water and organic solvents such as lower alcohol (e.g. ethanol and acetone). The composition can, if desired, contain additional ingredients such as deodorizing agents, fragrances, surfactants, buffering agents, and the like. Additionally, known antimicrobial agents such as alkyl dimethyl benzyl ammonium chloride can be included in the composition.

When contemplating the use of an antimicrobial composition of this invention against *P. acnes*, the composition may include acceptable carriers and diluents with which the composition is administered. A particularly preferred mode of administration is via topical route. Thus, the composition may be applied topically in the form of a lotion, solution, cream, ointment or dusting powder.

For example, the composition may be formulated into a cream consisting of an aqueous emulsion of polyethylene glycols or liquid paraffin; or it may be incorporated at a concentration between 1 and 10%, into an ointment consisting of a white wax or white soft paraffin base together with such stabilizers and preservatives as may be required. The topical compositions can, if desired, contain additional ingredients such as binders, excipients, antioxidants, and dyes.

The present invention is illustrated by the following examples. However, it should be understood that the invention is not limited to the specific details of these examples.

GENERAL ANTIMICROBIAL ASSAY PROCEDURE

Chemicals

Anacardic acids were isolated from cashew nut shell oil according to the published procedure of I. Kubo et al., *J. Agric. Food Chem.*, 34, 970 (1986). Indole, farnesol, limonene, citronellol, and β-caryophyllene were available from Sigma Chemical Co. (St. Louis, Mo.). β-Pinene was available from Aldrich Chemical Company (Milwaukee Wis.). Hinokitiol and longifolene were available from Takasago International Corporation (Tokyo, Japan). Pine resin (oleoregin) was obtained from the core of live pine trees, *Pinus ponderosa*.

Microorganisms

*Pseudomonas aeruginosa* (ATCC 25619) and *Propionibacterium acnes* (ATCC 11827) were obtained from the American Type Culture Collection, Rockville, Md.

Assay

Against *P. aeruginosa*

Minimum Inhibition Concentration (MIC) was determined by a broth macro dilution method. The media used in this assay contain nutrient broth (0.8%), yeast extract (0.5%), and glucose (0.1%). Each 100 mg of a test sample was dissolved in 1 ml dimethyl formamide (DMF) to provide a concentration of 100 mg/ml of a sample solution. Twofold serial dilutions were conducted by adding an aliquot of the sample solution to an equal volume of DMF. A diluted test sample solution (30 µl) was added to 3 ml of a culture medium followed by further addition of 60 µof a bacterial culture. The mixture was incubated at 30°–32° C. for 48 hours. The turbidity of the incubated culture was measured at 660 nm. MIC is a lowest concentration of the test sample required to completely inhibit the growth of the bacteria.

Against *P. acnes*

Minimum Inhibition Concentration (MIC) was determined by a broth macro dilution method in a similar manner to that described above. The media used in this assay contain Actinomyces broth (5.7%). The incubation was carried out anaerobically at 37° C., 48 hours.

Antimicrobial Activity

The MIC's of indole and individual naturally occurring substances were determined against *P. aeruginosa* and/or against *P. acnes*. Results are shown below.

| Compound | MIC µg/ml |
|---|---|
| *P. aeruainosa* | |
| Indole | 1000 |
| Anacardic acid | >1000 |
| Limonene | >2000 |
| β-Pinene | >2000 |
| Farnesol | >2000 |
| Citronellol | >2000 |
| Pine resin | >1000 |
| *P. acnes* | |
| Indole | 500 |
| Anacardic acid | 3.9 |
| Limonene | 62.5 |
| A-Pinene | 125 |

-continued

| Compound | MIC μg/ml |
| --- | --- |
| Farnesol | 7.8 |
| β-Citronellol | 500 |
| Longifolene | 7.8 |
| β-Caryophylene | 7.8 |

EXAMPLE 1

MIC'S of Naturally Occurring Substances in Combination with Indole Against *P. aeruginosa*

The MIC's of naturally occurring substances were determined when 250 μg/ml of indole was present in addition to specific naturally occurring substances. Results are shown below.

| Compound | MIC μg/ml |
| --- | --- |
| Anacardic acid | 3.9 |
| Cintronellol | 250 |
| Limonene | 62.5 |
| Isoeugenol | 500 |
| β-Pinene | 62.5 |
| Farnesol | 31.2 |
| Hinokitiol | 12.5 |
| Pine Resin | 7.8 |

These data show that addition of indole markedly enhances the antimicrobial activity (against *P. aeruginosa*) of the natural compounds tested.

EXAMPLE 2

MIC's of Naturally Occurring Substances in Combination with Indole Against *P. acnes*

The MIC's of naturally occurring substances were determined when 250 μg/ml of indole was present in addition to specific naturally occurring substances. Results are shown below.

| Compound | MIC μg/ml |
| --- | --- |
| Longifolene | 0.49 |
| β-Caryophyllene | 0.49 |
| Anacardic acid | 0.98 |
| Limonene | 1.95 |
| Farnesol | 1.9 |
| β-Pinene | 31.2 |
| Citronellol | 62.5 |

The MIC's of some selected naturally occurring substances were determined when 125 μg/ml of indole was present in addition to specific naturally occurring substances. Results are shown below.

| Compound | MIC μg/ml |
| --- | --- |
| Anacardic acids | 1.95 |
| Limonene | 31.2 |

These results show that addition of indole markedly enhances the antimicrobial activity (against *P. acnes*) of the natural compounds tested.

EXAMPLE 3

Disinfectant Formulation

The following ingredients were combined in the following proportions by weight:

| INGREDIENT | w/w % |
| --- | --- |
| Indole | 1.0 |
| Anacardic acid | 0.05 |
| Ethanol | 1.8 |
| i-Propyl alcohol | 0.9 |
| Xylenol | 1.5 |
| Fragrance | 1.0 |
| Soap | 15.0 |
| Water | remaining part |

The mixture was blended uniformly to produce a disinfectant formulation. The formulation can be further diluted with water for cleaning purposes. The disinfectant formulation was effective against *P. aeruginosa*.

EXAMPLE 4

Detergent Formulation

The following ingredients were combined in the following proportions by weight:

| INGREDIENT | w/w % |
| --- | --- |
| Indole | 1 |
| Pine resin | 0.1 |
| White protopet 1s | 6 |
| Alkyl aryl polyether sulfonate | 50 |
| Cholesterol | 2 |
| Water | remaining part |

The mixture was uniformly blended to produce a detergent formulation. The detergent formulation was effective against *P. aeruginosa*.

EXAMPLE 5

Shampoo Formulation

The following ingredients were combined in the following proportions by weight:

| INGREDIENT | w/w % |
| --- | --- |
| Indole | 0.15 |
| TEA lauryl sulfate | 18.0 |
| Hydroxyproxyl methylcellulose | 15.0 |
| Ammonium lauryl sulfate | 8.0 |
| Cocamide | 4.0 |
| Palmitic acid | 0.3 |
| DMDM Hydantoin | 0.15 |
| Tetra sodium ethylene diamine | 0.05 |
| Citric acid | small quantity |
| Sodium chloride | small quantity |
| β-Citronellol and limonene | 0.85 |
| Water | remaining part |

The mixture was uniformly blended to produce a shampoo formulation. The shampoo formulation was effective against *P. aeruginosa*.

EXAMPLE 6

Disinfectant Formulation

The following ingredients were combined in the following proportions by weight:

| INGREDIENT | w/w % |
|---|---|
| Indole | 0.2 |
| β-Caryophyllene | 0.2 |
| Sodium alkyl sulfate | 5.0 |
| Sodium lauryl sulfate | 5.0 |
| Glycerin | 10.0 |
| Water | remaining part |

The mixture was uniformly blended to produce a disinfectant formulation.

The MIC of the above disinfectant formulation against *P. acnes* was determined according to the assay procedure described earlier. For comparative purposes, the MIC of a disinfectant formulation which does not contain either indole or β-caryophyllene was determined. Results are shown below.

| | MIC (μg/ml) |
|---|---|
| The disinfectant solution of this invention | 100 |
| A disinfecting solution containing neither indole nor β-caryophyllene | 1,000 |

The disinfectant formulation of this invention was 10-fold more active than the formulation without indole and β-caryophyllene.

EXAMPLE 7

Lotion Formulation

The following ingredients were combined in the following proportions by weight:

| INGREDIENT | w/w % |
|---|---|
| Indole | 0.2 |
| β-Caryophyllene | 0.2 |
| Sorbitol | 5.0 |
| Glycerin | 20.0 |
| Water | remaining part |

The mixture was uniformly blended to produce a lotion formulation. The MIC of the above lotion against *P. acnes* was determined according to the assay 15 procedure described earlier. For comparative purposes, the MIC of a lotion formulation which does not contain either indole or β-caryophyllene. Results are shown below.

| | MIC (μg/ml) |
|---|---|
| The lotion formulation of this invention | 100 |
| A disinfecting solution containing neither indole nor β-caryophyllene | 100,000 |

The lotion formulation of this invention was 1000-fold more active than the formulation without indole and β-caryophyllene.

EXAMPLE 8

Cream Formulation

The following ingredients were combined in the following proportions by weight:

| INGREDIENT | w/w % |
|---|---|
| Indole | 0.2 |
| Limonene | 0.2 |
| Butanediol | 5.0 |
| Beeswax | 2.0 |
| Lanolin | 10.0 |
| Squalene | 30.0 |
| Paraoxyethylenesorbitan monolauryl acid ester | 2.0 |
| Water | remaining part |

The mixture was uniformly blended to produce a cream formulation. The cream formulation was effective as an anti-acne agent.

The invention now being fully described, it will be apparent to one of ordinary skill in the art that many changes and modifications can be made without departing from the spirit or scope of the invention.

We claim:

1. A method for enhancing the antimicrobial activity of a naturally occurring substance against *P. aeruginosa*, which comprises the steps of:

(a) combining a formulation consisting essentially of a naturally occurring substance, a carrier suitable for household, pharmaceutical or cosmetic use, and an antimicrobially enhancing amount of indole, wherein the naturally occurring substance is selected from the group consisting of anacardic acid, limonene, β-pinene, farnesol, β-citronellol, pine resin, and hinokitiol and the antimicrobially enhancing amount of indole is about 0.2 to about 100 parts by weight based on one part of the naturally occurring substance; and (b) applying the combined mixture to a host or environment infected with *P. aeruginosa*.

2. A method for enhancing the antimicrobial activity of a naturally occurring substance against *P. acnes*, which comprises the steps of: (a) combining a formulation consisting essentially of a naturally occurring substance, a pharmaceutically or cosmetically acceptable carrier, and an antimicrobially enhancing amount of indole, wherein the naturally occurring substance is selected from the group consisting of anacardic acid, limonene, β-pinene, farnesol, β-citronellol, longifolene, and β-caryophyllene; and the antimicrobially enhancing amount of indole is about 1 to about 1000 parts by weight based on one part of the naturally occurring substance; and (b) applying the combined mixture to a host.

* * * * *